US009828320B2

(12) United States Patent
Hintzer et al.

(10) Patent No.: US 9,828,320 B2
(45) Date of Patent: Nov. 28, 2017

(54) METHODS OF MAKING HALOGENATED FLUORINATED ETHER-CONTAINING COMPOUNDS

(71) Applicant: 3M Innovative Properties Company, St. Paul, MN (US)

(72) Inventors: Klaus Hintzer, Kastl (DE); Markus E. Hirschberg, Burgkirchen (DE); Kai Helmut Lochhaas, Neuotting (DE); Werner Schwertfeger, Langgoens (DE); Oleg Shyshkov, Burgkirchen (DE); Arne Thaler, Emmerting (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/529,104

(22) PCT Filed: Nov. 20, 2015

(86) PCT No.: PCT/US2015/061723
§ 371 (c)(1),
(2) Date: May 24, 2017

(87) PCT Pub. No.: WO2016/089617
PCT Pub. Date: Jun. 9, 2016

(65) Prior Publication Data

US 2017/0260116 A1 Sep. 14, 2017

Related U.S. Application Data

(60) Provisional application No. 62/085,696, filed on Dec. 1, 2014.

(51) Int. Cl.

| | |
|---|---|
| *C07C 41/14* | (2006.01) |
| *C07C 45/44* | (2006.01) |
| *C07C 45/51* | (2006.01) |
| *C07C 253/10* | (2006.01) |
| *C07C 407/00* | (2006.01) |
| *C07C 303/30* | (2006.01) |

(52) U.S. Cl.
CPC .............. *C07C 41/14* (2013.01); *C07C 45/44* (2013.01); *C07C 45/518* (2013.01); *C07C 253/10* (2013.01); *C07C 303/30* (2013.01); *C07C 407/00* (2013.01)

(58) Field of Classification Search
CPC ....... C07C 41/14; C07C 407/00; C07C 45/44; C07C 45/518; C07C 253/10; C07C 303/30
See application file for complete search history.

(56) References Cited

U.S. PATENT DOCUMENTS

| | | | | |
|---|---|---|---|---|
| 3,250,807 | A * | 5/1966 | Fritz | C07C 51/62 204/157.63 |
| 5,278,340 | A | 1/1994 | Koike | |
| 2002/0160272 | A1 | 10/2002 | Tanaka | |
| 2011/0245520 | A1 | 10/2011 | Zipplies | |
| 2017/0066877 | A1 | 3/2017 | Hintzer | |

FOREIGN PATENT DOCUMENTS

| | | |
|---|---|---|
| DE | 1104968 | 4/1961 |
| WO | WO 2013-097477 | 7/2013 |

OTHER PUBLICATIONS

Blancou, "Reactivity of Perfluorohalogenoalkanes in the Presence of Metallic Couples. Reactivity of Perfluoroiodoalkanes on Halogenated Derivatives in Dissociating Aprotic Solvents (DMSO, DMF)", Journal of Fluorine Chemistry, 1982, vol. 20, pp. 255-265.
Brandwood, "Some Reactions of Polyfluoroalkyl Ethers and the Preparation of Bis (Trifluorovinyl) Ether", Journal of Fluorine Chemistry, 1975, vol. 06, pp. 37-57.
Cao, "Practical and Efficient Synthesis of Perfluoroalkyl Iodides From Perfluoroalkyl Chlorides Via Modified Sulfinatodehalogenation", Journal of Fluorine Chemistry, 2007, vol. 128, pp. 1187-1190.
Huang, "Studies on Deiodo-Sulfination Part—II the Reactions of Perfluoroalkanesulfinates With Halogen and Halogen Acids and a New Method for the Synthesis of Perfluorosulfonic Acid", Journal of Fluorine Chemistry, 1983, vol. 23, pp. 229-240.
Krespan, "Derivatives of Functionalized Fluoro Esters and Fluoro Ketones. New Fluoro Monomer Syntheses", Journal of Organic Chemistry, 1986, vol. 51, pp. 326-332.
Peng, "Fluorinated Sulfonate Surfactants", Journal of Fluorine Chemistry, 2012, vol. 133, pp. 77-85.
Yamabe, "Novel Phosphonated Perfluorocarbon Polymers", European Polymer Journal, 2000, vol. 36, pp. 1035-1041.
International Search Report for PCT International Application No. PCT/US2015/061723, dated Feb. 16, 2016, 3 pages.

* cited by examiner

*Primary Examiner* — Rosalynd A Keys
(74) *Attorney, Agent, or Firm* — Julie Lapos-Kuchar

(57) ABSTRACT

Described herein are three methods for making halogenated fluorinated ether-containing compounds using a fluorinated olefin or hexafluoropropylene oxide.

20 Claims, No Drawings

METHODS OF MAKING HALOGENATED FLUORINATED ETHER-CONTAINING COMPOUNDS

CROSS REFERENCE TO RELATED APPLICATIONS

This application is a national stage filing under 35 U.S.C. 371 of PCT/US2015/061723, filed Nov. 20, 2015, which claims the benefit of U.S. Application No. 62/085,696, filed Dec. 1, 2014, the disclosure of which is incorporated by reference in its/their entirety herein.

TECHNICAL FIELD

Methods of making halogenated fluorinated ether-containing compounds are disclosed.

BACKGROUND

Bromine/iodine-containing compounds are key-materials for producing peroxide curable elastomers. They are used as chain transfer agents and/or as cure site monomers. For example, diiodoperfluorobutane [$I(CF_2)_4I$] is one of the most used chain transfer agent and could be used as a precursor for a cure site monomer (e.g., an iodo compound comprising a terminal double bond).

Bromine/iodine containing acid fluorides are also valuable precursors to produce the vinyl or allyl ethers which can be used as cure site monomers in making elastomers as well as long-chain-branching compounds for a variety of applications.

SUMMARY

There is a desire for alternative and/or new compounds that can be used as chain transfer agents or cure site monomers in the synthesis of fluoropolymers. There is also a desire for new methods of manufacture of compounds that can be used as chain transfer agents or cure site monomers that are less expensive and/or use readily available starting materials such as, for example, fluorosulfonic acid ($FSO_3H$), tetrafluoroethylene (TFE), hexafluoropropylene oxide (HFPO), elemental halogens, and interhalogens.

In one aspect, a method of making a halogenated fluorinated ether-containing compound from a fluoroolefin is described, the method comprising:

(i) halogenating a difluorosulfuryl peroxide followed by reaction with a first fluoroolefin to form a halogenated fluoroorganyl acid fluoride;

(ii) reacting the halogenated fluoroorganyl acid fluoride with a first compound selected from at least one of:

(a) a second fluoroolefin in the presence of a halogen containing compound to form the halogenated fluorinated ether-containing compound; and (b) HFPO to form a corresponding acid fluoride and converting the corresponding acid fluoride into the halogenated fluorinated ether-containing compound.

In another aspect, a method of making a halogenated fluorinated ether-containing compound from a fluoroolefin is described, the method comprising:

(i) forming 2,2,3,3-tetrafluoro-3-halogenopropanenitrile using a cyanide containing compound and TFE wherein the forming is selected from:

a) adding XCN to TFE wherein X is I, Br or Cl; and b) adding MCN to TFE wherein M is an alkali metal followed by contact with a halogen containing compound;

(ii) converting the 2,2,3,3-tetrafluoro-3-halogenopropanenitrile in 2,2,3,3-tetrafluoro-3-halogenopropanoyl fluoride;

(iii) reacting the 2,2,3,3-tetrafluoro-3-halogenopropanoyl fluoride with a first compound selected from at least one of:

(a) a fluoroolefin in the presence of a halogen containing compound to form the halogenated fluorinated ether-containing compound; and (b) HFPO to form the corresponding acid fluoride and converting the corresponding acid fluoride into a halogenated fluorinated ether-containing compound.

In yet another aspect, a method of making halogenated fluorinated ether-containing compound is described, the method comprising:

(i) reacting a perfluoroorganyl diacid difluoride with a first compound selected from at least one of (a) a first fluoroolefin in the presence of a halogen containing compound to form the halogenated fluorinated ether-containing compound; and (b) HFPO to form the corresponding diacid difluoride and converting the corresponding diacid difluoride into the halogenated fluorinated ether-containing compound.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more;

"and/or" is used to indicate one or both stated cases may occur, for example A and/or B includes, (A and B) and (A or B);

"fluoroolefin" is an aliphatic compound comprising at least one terminal carbon-carbon double bond (e.g., alkene or polyene). The fluoroolefin is fluorinated, meaning that at least one of the carbon-hydrogen bonds is replaced with a carbon-fluorine bond. The fluoroolefin may be partially fluorinated (wherein the compound comprises at least one carbon-hydrogen bond and at least one carbon-fluorine bond) or fully fluorinated (wherein the compound comprises carbon-fluorine bonds and no carbon-hydrogen bonds). Exemplary fluoroolefins are selected from at least one of tetrafluoroethylene (TFE), hexafluoropropylene (HFP), vinylidene fluoride (VDF), and chlorotrifluoroethylene (CTFE);

"halogen containing compound" is selected from elemental halogens ($I_2$, $Br_2$ or $Cl_2$) or interhalogens; and "interhalogen" refers to a compound comprising at least two or more different halogens, e.g., having the formula $XY_n$ where n is an odd numbered integer from 1-7 and X and Y are halogens with X being the less electronegative halogen, such as for example, IF and ICl.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Described herein are methods of making a halogenated fluorinated ether-containing compound using a fluoroolefin or HFPO (hexafluoropropylene oxide).

Method I

The Method I synthesis starts with a difluorosulfuryl peroxide. Difluorosulfuryl peroxide ($FO_2SO$—$OSO_2F$) can be prepared electrochemically using fluorosulfonic acid ($FSO_3H$).

The difluorosulfuryl peroxide is halogenated by reaction with a halogen containing compound at a temperature of at least 10, 20, 23, 25, 30, or even 35° C.; and at most 40, 50, 60, or even 80° C. Generally, at least a mole equivalent of the difluorosulfuryl peroxide to the halogen in the halogen containing compound should be used to favor the formation of the products. Then, a first fluoroolefin is introduced to form a halogenated fluoroorganyl acid fluoride via the corresponding fluorosulfate as intermediate. This reaction may occur in situ or can be pushed to favor the conversion to the acid fluoride by introducing suitable sources of fluoride such as, for example, alkaline fluorides (MF), alkaline earth fluorides ($MF_2$), or tetra-organylammonium fluorides. In one embodiment, the reaction may be conducted at a temperature of at least 10, 20, 23, 25, 30, or even 35° C.; and at most 40, 50, 60, 80, or even 100° C. Within this reaction, the intermediately generated halogenated olefin containing fluorosulfate (for example I—$CF_2CF_2$—$OSO_2F$) is converted in the presence of a small amount of fluoride to the corresponding halogenated fluoroorganyl acid fluoride. The amount of fluoride used lies in the range of 0.03 to 10 mol % moles of the fluoride ion to moles —$OSO_2F$. Alternatively, the intermediately generated halogenated olefin containing fluorosulfate could be isolated by distillation and subsequently reacted with a small amount of fluoride (0.03 to 10 mol %)—to the corresponding fluoroorganyl halogenated acid fluoride. The resulting halogenated fluoroorganyl acid fluoride compound may be isolated and purified by known methods.

The halogenated fluoroorganyl acid fluoride is for example of the structure $XCF_2C(O)F$ or $XCF(CF_3)C(O)F$ with X=I, Br, or Cl.

The halogenated fluoroorganyl acid fluoride is then reacted with either a second fluoroolefin or HFPO.

If the halogenated fluoroorganyl acid fluoride is reacted with a second fluoroolefin, it is done in the presence of a halogen containing compound to form the halogenated fluorinated ether-containing compound. The reaction is conducted preferably at a temperature in the range of −40 to +60° C. depending on the catalyst used. The reaction is preferably conducted in non-reactive organic solvent, for example those which have a boiling point up to 275° C. (e.g. triglyme and tetraglyme), preferably those having a boiling point up to 170° C. (e.g. $CH_3CN$, tetrahydrofuran, propionitrile, monoglyme, diglyme) or mixtures thereof. The molar ratio of the halogenated fluoroorganyl acid fluoride to the second fluoroolefin is in the range of 1:0.5 to 1:5, preferably in the range of 1:1.1 to 1:1.2.

If the halogenated fluoroorganyl acid fluoride is reacted with HFPO, it forms the corresponding acid fluoride which is then converted into the halogenated fluorinated ether-containing compound. The reaction of the halogenated fluoroorganyl acid fluoride with HFPO occurs by contacting the compounds preferably at a temperature in the range of −40 to +60° C. depending on the catalyst used, in non-reactive organic solvents which have a boiling point up to 275° C. (e.g. triglyme and tetraglyme), preferably those having a boiling point up to 170° C. (e.g., $CH_3CN$, tetrahydrofuran, propionitrile, monoglyme, diglyme) or mixtures thereof. The molar ratio of the halogenated fluoroorganyl acid fluoride to HFPO is in the range of 1:0.5 to 1:5, preferably in the range of 1:1.1 to 1:1.2.

The corresponding acid fluoride can be converted into the halogenated fluorinated ether-containing compound using a variety of processes.

In a first embodiment, the corresponding acid fluoride is reacted with a third fluoroolefin in the presence of a halogen containing compound to form the halogenated fluorinated ether-containing compound. The reaction is conducted at a temperature in the range of −40 to +60° C. depending on the catalyst used, in non-reactive organic solvents which have a boiling point up to 275° C. (e.g. triglyme and tetraglyme), preferably those having a boiling point up to 170° C. (e.g., $CH_3CN$, tetrahydrofuran, propionitrile, monoglyme, diglyme) or mixtures thereof.

In a second embodiment, the corresponding acid fluoride is pyrolized in the presence of alkali carbonate (e.g. $Na_2CO_3$, $K_2CO_3$) to form a vinyl ether. The pyrolysis occurs at 120 to 300° C., preferably at 150 to 180° C. The resulting vinyl ether then can be reacted with an interhalogen to form the halogenated fluorinated ether-containing compound. For example, the reaction of the resulting vinyl ether occurs with a mixture of elemental iodine and iodine pentafluoride at a temperature in the range of 30° C. to 200° C., preferably at a temperature in the range of 80 to 160° C. Alternatively, the reaction of the resulting vinyl ether could be conducted with ICl, HF, and $BF_3$ at about 50° C. as is known in the art (see for example see *J. Fluorine Chem.* 2012, 133, 77-85).

In a third embodiment, the corresponding acid fluoride is reacted with perfluoroallyl fluorosulfate ($CF_2$=CF—$CF_2$—$OSO_2F$) to form the halogenated fluorinated ether-containing compound. The reaction is conducted preferably at a temperature in the range of −40 to +60° C. depending on the fluoride containing catalyst (e.g. alkaline fluorides (MF), alkaline earth fluorides ($MF_2$), or tetra-organylammonium fluorides) used. The reaction is preferably conducted in non-reactive organic solvent, for example those which have a boiling point up to 275° C. (e.g. triglyme and tetraglyme), preferably those having a boiling point up to 170° C. (e.g. $CH_3CN$, tetrahydrofuran, propionitrile, monoglyme, diglyme) or mixtures thereof.

In a fourth embodiment, the corresponding acid fluoride is reacted with LiI to form the iodinated fluorinated ether-containing compound at a temperature in the range of 100 to 250° C. preferably in the absence of any solvents.

Optionally, in one embodiment, the corresponding acid fluoride is reacted with HFPO to form an elongated acid fluoride which can then be converted into the halogenated fluorinated ether-containing compound using the methods described above.

Alternatively, if a carboxylic acid containing molecule is desired, the corresponding acid fluoride can be hydrolyzed, at a temperature in the range of 0 to 100° C., preferably 20-70° C., to form a corresponding carboxylic acid.

The halogenated fluorinated ether-containing compounds of Method I are of the following formulas:

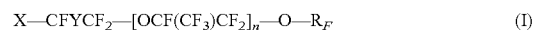

$$X\text{—}CFYCF_2\text{—}[OCF(CF_3)CF_2]_n\text{—}O\text{—}R_F \quad (I)$$

wherein X is selected from Br, Cl and I; Y is F or $CF_3$; n is an integer from 0-3 and $R_F$ is —CF=$CF_2$ or —$CF_2CF$=$CF_2$; and

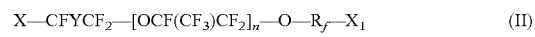

$$X\text{—}CFYCF_2\text{—}[OCF(CF_3)CF_2]_n\text{—}O\text{—}R_f\text{—}X_1 \quad (II)$$

wherein X and $X_1$ are independently selected from Br, Cl and I; Y is F or $CF_3$; $R_f$ is selected from —$CF_2CF_2$—, —$CF(CF_3)CF_2$—, —$CFClCF_2$—, or —$CH_2CF_2$—; and n is an integer from 0-3.

Exemplary halogenated fluorinated ether containing compounds made by Method I include: I—$CF_2$—$CF_2$—O—

CF=CF$_2$, I—CF$_2$—CF$_2$—O—CF$_2$—CF=CF$_2$, I—CF(CF$_3$)—CF$_2$—O—CF=CF$_2$, I—CF(CF$_3$)—CF$_2$—O—CF$_2$—CF=CF$_2$, I—CF$_2$—CF$_2$—O—CF(CF$_3$)—CF$_2$—O—CF=CF$_2$, I—CF$_2$—CF$_2$—O—CF(CF$_3$)—CF$_2$—O—CF$_2$—CF=CF$_2$, I—CF$_2$—CF$_2$—(O—(CF(CF$_3$)—CF$_2$)$_2$—O—CF=CF$_2$, I—CF$_2$—CF$_2$—(O—(CF(CF$_3$)—CF$_2$)$_2$—O—CF$_2$—CF=CF$_2$, I—CF$_2$—CF$_2$—O—CF$_2$—CF$_2$—I, I—CF(CF$_3$)—CF$_2$—O—CF$_2$—CF$_2$—I, I—CF$_2$—CF$_2$—O—CF(CF$_3$)—CF$_2$—O—CF$_2$—CF$_2$—I, I—(CF(CF$_3$)—CF$_2$—O)$_2$—CF$_2$—CF$_2$—I, Br—CF$_2$—CF$_2$—O—CF=CF$_2$, Br—CF$_2$—CF$_2$—O—CF$_2$—CF=CF$_2$, Br—CF(CF$_3$)—CF$_2$—O—CF=CF$_2$, Br—CF$_2$—CF$_2$—O—CF$_2$—CF$_2$—Br, I—CF$_2$—CF$_2$—O—CF$_2$—CF$_2$—Br, and Br—CF(CF$_3$)—CF$_2$—O—CF$_2$—CF$_2$—I.

Halogenated fluorinated ether containing compounds of Formula I can be obtained for example, by the reaction of a halogenated fluoroorganyl acid fluoride with HFPO to an elongated halogenated fluoroorganyl acid fluoride followed by subsequent pyrolysis or by the reaction of a halogenated fluoroorganyl acid fluoride with CF$_2$=CF—CF$_2$—OSO$_2$F. Halogenated fluorinated ether containing compounds of Formula II can be obtained for example, by the reaction of a halogenated fluoroorganyl acid fluoride with a fluoroolefin in presence of a halogen containing compound. Furthermore, molecules of formula I can be converted to formula II by fluoroiodination.

Method II

The Method II synthesis starts with a cyanide-containing compound that is reacted with tetrafluoroethylene and a halogen to form 2,2,3,3-tetrafluoro-3-halogenopropanenitrile (in other words, NCCF$_2$CF$_2$X where X is I, Cl, or Br). The cyanide-containing compound is XCN or MCN, wherein X is I, Br or Cl and M is an alkali metal (e.g., Li, Na, K, etc.).

In one embodiment, XCN is contacted with tetrafluoroethylene to form the 2,2,3,3-tetrafluoro-3-halogenopropanenitrile. This reaction occurs in non-reactive organic solvents which have a boiling point up to 275° C. (e.g. triglyme and tetraglyme), preferably those having a boiling point up to 170° C. (e.g., CH$_3$CN, tetrahydrofuran, propionitrile, monoglyme, diglyme), or mixtures thereof.

In another embodiment, MCN is first contacted with tetrafluoroethylene in the presence of a solvent and then this product is subsequently contacted without previous isolation with a halogen containing compound to form the 2,2,3,3-tetrafluoro-3-halogenopropanenitrile. This 'one-pot reaction' may be conducted at a temperature of at least 10, 20, 23, 25, 30, or even 35° C.; and at most 70° C. in non-reactive organic solvents which have a boiling point up to 275° C. (e.g. triglyme and tetraglyme), preferably those having a boiling point up to 170° C. (e.g., CH$_3$CN, tetrahydrofuran, propionitrile, monoglyme, diglyme) or mixtures thereof. This reaction can be promoted in the presence of Lewis acids as a catalyst (for example, BF$_3$ or BF$_3$.THF).

After forming the 2,2,3,3-tetrafluoro-3-halogenopropanenitrile, the 2,2,3,3-tetrafluoro-3-halogenopropanenitrile is hydrolyzed to form 2,2,3,3-tetrafluoro-3-halogenopropanoic acid. The hydrolysis occurs at a temperature in the range of 0 to 100° C. in the presence of water and/or with an aqueous sodium or potassium hydroxide solution and subsequent addition of an acid.

2,2,3,3-tetrafluoro-3-halogenopropanoic acid is then converted into 2,2,3,3-tetrafluoro-3-halogenopropanoyl fluoride which is done either by direct conversion or via the intermediate 2,2,3,3-tetrafluoro-3-halogenopropanoyl chloride.

The direct conversion of 2,2,3,3-tetrafluoro-3-halogenopropanoic acid into 2,2,3,3-tetrafluoro-3-halogenopropanoyl fluoride is conducted for example with fluorinating agents such as trifluoromethylated and difluorochloromethylated benzenes (e.g. C$_6$H$_5$CF$_3$, C$_6$H$_5$CF$_2$Cl) in the presence of Lewis Acid catalysts (e.g. a mixture of TiO$_2$ and TiCl$_4$; BF$_3$). Also diethylaminosulfur trifluoride and 2-chloro-1,1,2-trifluoroethyl(diethyl)amine are suitable fluorinating agents for the direct conversion.

The intermediate 2,2,3,3-tetrafluoro-3-halogenopropanoyl chloride can be prepared from 2,2,3,3-tetrafluoro-3-halogenopropanoic acid with for example thionyl chloride, benzoylchloride, or oxalyl dichloride. In the next step, 2,2,3,3-tetrafluoro-3-halogenopropanoyl chloride is reacted with a source of fluoride to form the 2,2,3,3-tetrafluoro-3-halogenopropanoyl fluoride. The source of the fluoride can be an inorganic fluoride salt such as for example alkali or an alkaline earth metal fluorides, or fluorine containing organic compounds like trifluoromethylated and difluorochloromethylated benzenes (e.g. C$_6$H$_5$CF$_3$, C$_6$H$_5$CF$_2$Cl) in the presence of Lewis Acid catalysts. Also diethylaminosulfur trifluoride and 2-chloro-1,1,2-trifluoroethyl(diethyl)amine are suitable fluorinating agents for this reaction.

The 2,2,3,3-tetrafluoro-3-halogenopropanoyl fluoride is then reacted with either a fluoroolefin or HFPO.

If the 2,2,3,3-tetrafluoro-3-halogenopropanoyl fluoride is reacted with a fluoroolefin, it is done in the presence of a halogen containing compound to form the halogenated fluorinated ether-containing compound. The reaction is conducted at preferably at a temperature in the range of −40 to +60° C. depending on the catalyst used, in non-reactive organic solvents which have a boiling point up to 275° C. (e.g. triglyme and tetraglyme), preferably those having a boiling point up to 170° C. (e.g., CH$_3$CN, tetrahydrofuran, propionitrile, monoglyme, diglyme) or mixtures thereof. The molar ratio of the halogenated fluoroorganyl acid fluoride to an olefin is in the range of 1:0.5 to 1:5, preferably in the range of 1:1.1 to 1:1.2.

If the 2,2,3,3-tetrafluoro-3-halogenopropanoyl fluoride is reacted with HFPO it forms the corresponding acid fluoride, which is then converted into the halogenated fluorinated ether-containing compound. The reaction of the 2,2,3,3-tetrafluoro-3-halogenopropanoyl fluoride with HFPO takes place preferably at a temperature in the range of −40 to +60° C. depending on the catalyst used, in non-reactive organic solvents which have a boiling point up to 275° C. (e.g. triglyme and tetraglyme), preferably those having a boiling point up to 170° C. (e.g., CH$_3$CN, tetrahydrofuran, propionitrile, monoglyme, diglyme) or mixtures thereof. The molar ratio of the halogenated fluoroorganyl acid fluoride to HFPO is in the range of 1:0.5 to 1:5, preferably in the range of 1:1.1 to 1:1.2.

The corresponding acid fluoride can be converted into the halogenated fluorinated ether-containing compound using a variety of processes as described above in Method I. For example, the corresponding acid fluoride is pyrolized in the presence of alkali carbonate (e.g. Na$_2$CO$_3$, K$_2$CO$_3$) to form a vinyl ether. The pyrolysis occurs at 120 to 300° C., preferably at 150 to 180° C. The resulting vinyl ether then can be reacted with an interhalogen to form the halogenated fluorinated ether-containing compound. For example, the reaction of the resulting vinyl ether occurs with a mixture of elemental iodine and iodine pentafluoride at a temperature in the range of 30° C. to 200° C., preferably at a temperature in the range of 80 to 160° C. Alternatively, the reaction of the resulting vinyl ether could be conducted with ICl, HF, and BF$_3$ at about 50° C.

The halogenated fluorinated ether-containing compounds made by Method II have the structure of:

$$X-CF_2CF_2CF_2-[OCF(CF_3)CF_2]_n-O-R_F \qquad (III)$$

wherein X is selected from I, Br and Cl; n is an integer from 0-3; and $R_F$ is $-CF=CF_2$ or $-CF_2CF=CF_2$; and $$X-CF_2CF_2CF_2-[OCF(CF_3)CF_2]_n-O-R_f-X_1 \qquad (IV)$$

wherein X and $X_1$ are independently selected from I, Br and Cl; $R_f$ is selected from $-CF_2CF_2-$, $-CF(CF_3)CF_2-$, $-CFClCF_2-$, or $-CH_2CF_2-$; and n is an integer from 0-3.

Exemplary halogenated fluorinated ether containing compounds made by method II include: $I-CF_2-CF_2-CF_2-O-CF=CF_2$, $I-CF_2-CF_2-CF_2-O-CF_2-CF=CF_2$, $I-CF_2-CF_2-CF_2-O-CF(CF_3)-CF_2-O-CF=CF_2$, $I-CF_2-CF_2-CF_2-O-CF(CF_3)-CF_2-O-CF_2-CF=CF_2$, $I-CF_2-CF_2-CF_2-(O-(CF(CF_3)-CF_2)_2-O-CF=CF_2$, $I-CF_2-CF_2-CF_2-O-(CF(CF_3)-CF_2-O)_2-CF_2-CF=CF_2$, $I-CF_2-CF_2-CF_2-O-CF_2-CF_2-I$, $I-CF_2-CF_2-CF_2-O-CF(CF_3)-CF_2-O-CF_2-CF_2-I$, $Br-CF_2-CF_2-CF_2-O-CF=CF_2$, $Br-CF_2-CF_2-CF_2-O-CF_2-CF=CF_2$, $Br-CF_2-CF_2-CF_2-O-CF_2-CF_2-I$, and $I-CF_2-CF_2-CF_2-O-CF_2-CF_2-Br$.

Halogenated fluorinated ether containing compounds of Formula III can be obtained for example, by the reaction of a halogenated fluoroorganyl acid fluoride with HFPO to an elongated halogenated fluoroorganyl acid fluoride followed by subsequent pyrolysis or by the reaction of a halogenated fluoroorganyl acid fluoride with $CF_2=CF-CF_2-OSO_2F$. Halogenated fluorinated ether containing compounds of Formula IV can be obtained for example, by the reaction of a halogenated fluoroorganyl acid fluoride with a fluoroolefin in presence of a halogen containing compound. Furthermore, molecules of formula III can be converted to formula IV by fluoroiodination.

Method III

The Method III synthesis starts with a perfluoroorganyl diacid difluoride which is reacted with either a fluoroolefin or HFPO.

The perfluoroorganyl diacid difluoride is a compound of the structure $F(O)C(CF_2)_nC(O)F$ with $n=0-4, 6$, and 8.

The perfluoroorganyl diacid difluoride is commercially available or can be synthesized by techniques known in the art.

For example, $FSO_2O-(CF_2CF_2)_n-OSO_2F$ wherein n is an integer of 1-5 can be made electrochemically, yielding a distribution of n's (especially n=1-5). The distribution of $FSO_2O-(CF_2CF_2)_n-OSO_2F$ primarily depends on the electric current strength (which itself depends on the current density and the surface of electrodes; e.g., 50 to 90 Amperes), the content of peroxide, the ratio peroxide to TFE, the reaction temperature (e.g., 35-60° C.), and the TFE-flow ratio (e.g., 90 to 300 g/h) which depends on the cell size. The resulting mixture of perfluoroorganyl bis(fluorosulfates) can be distilled and the desired fraction collected and subsequently used. For example, the boiling point for the largest fractions of $FSO_2O-(CF_2CF_2)_n-OSO_2F$ are: n=1 is 101 to 103° C. at ambient pressure; n=2 is 136 to 137° C.; n=3 is 173 to 174° C.; n=4 is 90° C. at 14 mbar; n=5: 115° C. at 14 mbar with little to no fractions wherein n>6, which are solids. Even numbered perfluoroorganyl diacid difluorides are synthesized by reacting $FSO_2O-(CF_2CF_2)_n-OSO_2F$ with a fluoride catalyst to form the corresponding diacid difluoride. Odd numbered perfluoroorganyl diacid difluorides are commercially available, for example by Exfluor Research Corporation, Round Rock, Tex. (e.g. $F(O)C-(CF_2)_3-C(O)F$) and SynQuest Laboratories, Inc., Alachua, Fla. (e.g., $F(O)C-(CF_2)-C(O)F$).

If the perfluoroorganyl diacid difluoride is reacted with a first fluoroolefin, it is done in the presence of a halogen containing compound to form the halogenated fluorinated ether-containing compound. The reaction is conducted at a temperature in the range of −40 to +60° C. depending on the fluoride containing catalyst (e.g. alkaline fluorides (MF), alkaline earth fluorides ($MF_2$), or tetra-organylammonium fluorides) used, in non-reactive organic solvents which have a boiling point up to 275° C. (e.g. triglyme and tetraglyme), preferably those which have a boiling point up to 170° C. (e.g. $CH_3CN$, THF, propionitrile, monoglyme, diglyme) or mixtures thereof. The molar ratio of the perfluoroorganyl diacid difluoride to the first fluoroolefin is in the range of 1:1 to 1:10, preferably in the range of 1:2 to 1:5.

If the perfluoroorganyl diacid difluoride is reacted with HFPO it forms the corresponding diacid difluoride, which is then converted into the halogenated fluorinated ether-containing compound. The reaction of the perfluoroorganyl diacid difluoride with HFPO takes preferably at a temperature in the range of −40 to +60° C. depending on the catalyst used, in non-reactive organic solvents which have a boiling point up to 275° C. (e.g. triglyme and tetraglyme), preferably those which have a boiling point up to 170° C. (e.g. $CH_3CN$, THF, propionitrile, monoglyme, diglyme) or mixtures thereof. The molar ratio of the halogenated fluoroorganyl diacid difluoride to HFPO is in the range of 1:1 to 1:10, preferably in the range of 1:2 to 1:5.

The corresponding diacid difluoride can be converted into the halogenated fluorinated ether-containing compound using a variety of processes as described above in Method I keeping in mind that since there are two acid fluorides in the corresponding diacid difluoride compounds, the stoichiometries would double those previously disclosed to ensure both acid fluorides are converted.

For example, the corresponding diacid difluoride is pyrolyzed in the presence of alkali carbonate (e.g. $Na_2CO_3$, $K_2CO_3$) to form a divinyl ether. The pyrolysis occurs at 120 to 300° C., preferably at 150 to 180° C. The resulting divinyl ether then can be reacted with an interhalogen to form the halogenated fluorinated ether-containing compound. For example, the reaction of the resulting divinyl ether occurs with a mixture of elemental iodine and iodine pentafluoride at a temperature in the range of 30° C. to 200° C., preferably at a temperature in the range of 80 to 160° C. Alternatively, the reaction of the resulting divinyl ether could be conducted with ICl, HF, and $BF_3$ at about 50° C.

The halogenated fluorinated ether-containing compounds made by Method III have the structure of:

$$X-R_F-[OCF(CF_3)CF_2]_m-O-(OCF_2)_o-[OCF(CF_3)CF_2]_n-O-R_{F'} \qquad (V)$$

wherein X is selected from I, Br and Cl; $R_F$ is $-CF_2CF_2-$ or $-CF_2CF_2CF_2-$; n is an integer from 0-3; m is an integer from 0-3; o is an integer from 2-6, 8, and 10; and $R_{F'}$ is $-CF=CF_2$ or $-CF_2CF=CF_2$; and $$X-R_F-[OCF(CF_3)CF_2]_m-O-(CF_2)_o-[OCF(CF_3)CF_2]_n-O-R_f-X_1 \qquad (VI)$$

wherein X and $X_1$ are independently selected from I, Br and Cl; $R_F$ is independently selected from $-CF_2-CF_2-$, $-CF(CF_3)CF_2-$, $-CFClCF_2-$, or $-CH_2CF_2-$; n is an integer from 0-3; m is an integer from 0-3; o is an integer from 2-6, 8, and 10.

Exemplary halogenated fluorinated ether containing compounds made by method III include: I—$CF_2$—$CF_2$—O—$(CF_2)_2$—O—CF=$CF_2$, I—$CF_2$—$CF_2$—O—$(CF_2)_3$—O—CF=$CF_2$, I—$CF_2$—$CF_2$—O—$(CF_2)_4$—O—CF=$CF_2$, I—$CF_2$—$CF_2$—O—$(CF_2)_2$—O—$CF_2$—CF=$CF_2$, I—$CF_2$—$CF_2$—O—$(CF_2)_3$—O—$CF_2$—CF=$CF_2$, I—$CF_2$—$CF_2$—O—$(CF_2)_2$—O—CF($CF_3$)$CF_2$—O—$CF_2$=$CF_2$, I—$CF_2$—$CF_2$—O—$(CF_2)_2$—O—CF($CF_3$)$CF_2$—O—$CF_2$—$CF_2$—$CF_2$, I—$CF_2$—$CF_2$—O—$(CF_2)_2$—O—$CF_2$—$CF_2$—I, I—$CF_2$—$CF_2$—O—$(CF_2)_3$—O—$CF_2$—$CF_2$—I, and I—$CF_2$—$CF_2$—O—$(CF_2)_4$—O—$CF_2$—$CF_2$—I, Br—$CF_2$—$CF_2$—O—$(CF_2)_2$—O—CF=$CF_2$, Br—$CF_2$—$CF_2$—O—$(CF_2)_3$—O—CF=$CF_2$, Br—$CF_2$—$CF_2$—O—$(CF_2)_4$—O—CF=$CF_2$, Br—$CF_2$—$CF_2$—O—$(CF_2)_2$—O—$CF_2$—CF=$CF_2$, Br—$CF_2$—$CF_2$—O—$(CF_2)_2$—O—$CF_2$—$CF_2$—Br, Br—$CF_2$—$CF_2$—O—$(CF_2)_3$—O—$CF_2$—$CF_2$—Br, and Br—$CF_2$—$CF_2$—O—$(CF_2)_4$—O—$CF_2$—$CF_2$—Br, Br—$CF_2$—$CF_2$—O—$(CF_2)_2$—O—$CF_2$—$CF_2$—I, Br—$CF_2$—$CF_2$—O—$(CF_2)_3$—O—$CF_2$—$CF_2$—I, and I—$CF_2$—$CF_2$—O—$(CF_2)_4$—O—$CF_2$—$CF_2$—Br.

Halogenated fluorinated ether containing compounds of Formula V can be obtained for example, by the reaction of a halogenated fluoroorganyl diacid difluoride with HFPO to form an elongated halogenated fluoroorganyl diacid difluoride followed by the subsequent pyrolysis or by the reaction of a halogenated fluoroorganyl diacid difluoride with $CF_2$=CF—$CF_2$—$OSO_2F$. Halogenated fluorinated ether containing compounds of Formula VI can be obtained for example, by the reaction of a halogenated fluoroorganyl diacid difluoride with a fluoroolefin in presence of a halogen containing compound. Furthermore, molecules of formula V can be converted to formula VI by fluoroiodination.

In one embodiment, the compounds as disclosed herein (e.g., those of Formulas II, IV, and VI) can be used in a fluoropolymer polymerization as a chain transfer agent. Generally, chain transfer agents are added to the polymerization to control the molecular weight of the growing polymer chain. Optionally, chain transfer agents can be converted into a cure site monomer (for example by adding ethylene and consecutive dehydrohalogenation to the corresponding olefin) for subsequent crosslinking. In one embodiment, the compounds as disclosed herein (e.g., those of Formulas I, III, and V) can be used in a fluoropolymer polymerization as a cure site monomer. Generally a cure site monomer is incorporated into the polymer during polymerization and are then used as sites to subsequently crosslink polymer chains.

The fluoropolymers may be obtained by polymerizing the halogenated fluorinated ether-containing compounds of the present disclosure in the presence of fluorinated olefinic monomers and optionally additional monomers. Known polymerization techniques including aqueous emulsion polymerization may be used.

The halogenated fluorinated ether-containing compounds of the present disclosure may be used in the polymerization of fluoropolymers such as: TFE/propylene copolymer, a TFE/propylene/VDF copolymer, a VDF/HFP copolymer, a TFE/VDF/HFP copolymer, a TFE/PMVE copolymer, a TFE/$CF_2$=$CFOC_3F_7$ copolymer, a TFE/$CF_2$=$CFOCF_3$/$CF_2$=$CFOC_3F_7$ copolymer, a TFE/ethyl vinyl ether (EVE) copolymer, a TFE/butyl vinyl ether (BVE) copolymer, a TFE/EVE/BVE copolymer, a VDF/$CF_2$=CF—$OC_3F_7$ copolymer, an ethylene/HFP copolymer, a TFE/HFP copolymer, a CTFE/VDF copolymer, a TFE/VDF copolymer, a TFE/VDF/PMVE/ethylene copolymer, and a TFE/VDF/$CF_2$=$CFO(CF_2)_3OCF_3$ copolymer.

In one embodiment of the present disclosure, the fluoropolymer of the present disclosure may be cured with peroxide curing agents including organic peroxides. In many cases it is preferred to use a tertiary butyl peroxide having a tertiary carbon atom attached to a peroxy oxygen.

The cured fluoropolymers are particularly useful as seals, gaskets, and molded parts in systems that are exposed to elevated temperatures and/or corrosive materials, such as in automotive, chemical processing, semiconductor, aerospace, and petroleum industry applications, among others.

Exemplary embodiments include:

Embodiment 1

A method of making a halogenated fluorinated ether-containing compound from a fluoroolefin, the method comprising:
(i) halogenating a difluorosulfuryl peroxide followed by reaction with a first fluoroolefin to form a halogenated fluoroorganyl acid fluoride;
(ii) reacting the halogenated fluoroorganyl acid fluoride with first compound selected from at least one of:
  (a) a second fluoroolefin in the presence of a halogen containing compound to form the halogenated fluorinated ether-containing compound; and
  (b) HFPO to form a corresponding acid fluoride and converting the corresponding acid fluoride into the halogenated fluorinated ether-containing compound.

Embodiment 2

The method of embodiment 1, wherein converting the corresponding acid fluoride is selected from:
(i) reacting the corresponding acid fluoride with a third fluoroolefin in the presence of a halogen containing compound to form the halogenated fluorinated ether-containing compound;
(ii) pyrolyzing the corresponding acid fluoride to form a vinyl ether; then reacting the vinyl ether with an interhalogen to form the halogenated fluorinated ether-containing compound;
(iii) reacting the corresponding acid fluoride with $CF_2$=CF—$CF_2$—$OSO_2F$ to form the halogenated fluorinated ether-containing compound; or
(iv) reacting the corresponding acid fluoride with LiI to form the halogenated fluorinated ether-containing compound.

Embodiment 3

The method of any one of the previous embodiments, wherein the first fluoroolefin is selected from at least one of tetrafluoroethylene, hexafluoropropylene, and chlorotrifluoroethylene.

Embodiment 4

The method of any one of the previous embodiments, wherein the second fluoroolefin is selected from at least one of tetrafluoroethylene, hexafluoropropylene, vinylidene fluoride, and chlorotrifluoroethylene.

Embodiment 5

The method of any one of embodiments 2-4, wherein the third fluoroolefin is selected from at least one of tetrafluoroethylene, hexafluoropropylene, vinylidene fluoride, and chlorotrifluoroethylene.

Embodiment 6

The method of any one of the previous embodiments, further comprising reacting the corresponding acid fluoride with HFPO to form an elongated acid fluoride, which is then converted into the halogenated fluorinated ether-containing compound.

Embodiment 7

The method of any one of the previous embodiments, wherein the halogenated fluorinated ether-containing compound has the structure selected from at least one of:

$$X—CFYCF_2—[OCF(CF_3)CF_2]_n—O—R_F \quad (I)$$

wherein X is selected from Br, Cl and I; Y is F or $CF_3$; n is an integer from 0-3 and $R_F$ is $CF=CF_2$ and $CF_2CF=CF_2$; and $$X—CFYCF_2—[OCF(CF_3)CF_2]_n—O—R_{F'}—X_1 \quad (II)$$

wherein X and $X_1$ are independently selected from Br, Cl and I; Y is F or $CF_3$; $R_{F'}$ is selected from $CF_2CF_2$, $CF(CF_3)CF_2$, $CFClCF_2$, or $CH_2CF_2$; and n is an integer from 1-3.

Embodiment 8

A method of making a halogenated fluorinated ether-containing compound from a fluoroolefin, the method comprising:
(i) forming 2,2,3,3-tetrafluoro-3-halogenopropanenitrile using a cyanide containing compound and TFE wherein the forming is selected from:
  a) adding XCN to TFE wherein X is I, Br or Cl; and
  b) adding MCN to TFE wherein M is an alkali metal followed by contact with a halogen containing compound;
(ii) converting the 2,2,3,3-tetrafluoro-3-halogenopropanenitrile to 2,2,3,3-tetrafluoro-3-halogenopropanoyl fluoride;
(iii) reacting the 2,2,3,3-tetrafluoro-3-halogenopropanoyl fluoride with a first compound selected from at least one of
  (a) a fluoroolefin in the presence of a halogen containing compound to form the halogenated fluorinated ether-containing compound and
  (b) HFPO to form the corresponding acid fluoride and converting the corresponding acid fluoride into a halogenated fluorinated ether-containing compound.

Embodiment 9

The method of embodiment 8, wherein the converting of the corresponding acid fluoride is selected from:
(a) reacting the corresponding acid fluoride with a second compound selected from at least one of (i) a third fluoroolefin in the presence of a halogen containing compound to form the corresponding halogenated ether-containing compound and (ii) HFPO to form the corresponding acid fluoride;
(b) pyrolizing the corresponding acid fluoride to form a vinyl ether; then reacting the vinyl ether with an interhalogen to form the halogenated fluorinated ether-containing compound;
(c) reacting the corresponding acid fluoride with $CF_2=CF—CF_2—OSO_2F$ to form the the halogenated fluorinated ether-containing compound; or
(d) reacting the corresponding acid fluoride with LiI to form the halogenated fluorinated ether-containing compound.

Embodiment 10

The method of embodiment 8 or 9, wherein the second fluoroolefin is selected from at least one of tetrafluoroethylene, hexafluoropropylene, vinylidene fluoride, and chlorotrifluoroethylene.

Embodiment 11

The method of any one of embodiments 8-10, wherein the third fluoroolefin is selected from at least one of tetrafluoroethylene, hexafluoropropylene, vinylidene fluoride, and chlorotrifluoroethylene.

Embodiment 12

The method of any one of embodiments 8-11, further comprising reacting the corresponding acid fluoride with HFPO to form an elongated acid fluoride, which is then converted into the halogenated fluorinated ether-containing compound

Embodiment 13

The method of any one of embodiments 8-12, wherein the halogenated fluorinated ether-containing compound has the structure selected from at least one of:

$$X—CF_2CF_2CF_2—[OCF(CF_3)CF_2]_n—O—R_F \quad (I)$$

wherein X is selected from I, Br and Cl, n is an integer from 0-3; and $R_F$ is $CF=CF_2$ and $CF_2CF=CF_2$; and $$X—CF_2CF_2CF_2—[OCF(CF_3)CF_2]_n—O—R_{F'}—X_1 \quad (II)$$

wherein X and $X_1$ are independently selected from I, Br and Cl; $R_{F'}$ is selected from $CF_2CF_2$, $CFClCF_2$, or $CH_2CF_2$; and n is an integer from 0-3.

Embodiment 14

A method of making halogenated fluorinated ether-containing compound from a fluoroolefin, the method comprising:
(i) reacting a perfluoroorganyl diacid difluoride with a first compound selected from at least one of
  (a) a first fluoroolefin in the presence of a halogen containing compound to form the halogenated fluorinated ether-containing compound; and
  (b) HFPO to form the corresponding diacid difluoride and converting the corresponding diacid difluoride into the halogenated fluorinated ether-containing compound.

Embodiment 15

The method of embodiment 14, wherein the converting step is selected from:

(i) reacting the corresponding diacid difluoride with a second compound selected from at least one of
(a) a second fluoroolefin in the presence of a halogen containing compound to form the halogenated fluorinated ether-containing compound and
(b) reacting the corresponding acid fluoride with HFPO to form an acid fluoride
(ii) pyrolizing the corresponding acid fluoride to form a vinyl ether; then reacting the vinyl ether with an interhalogen to form the halogenated fluorinated ether-containing compound;
(iii) reacting the corresponding acid fluoride with $CF_2$=CF—$CF_2$—$OSO_2F$ to form the halogenated fluorinated ether-containing compound; or
(iv) reacting the corresponding acid fluoride with LiI to form the halogenated fluorinated ether-containing compound.

Embodiment 16

The method of any one embodiments 14-15, wherein the first fluoroolefin is selected from at least one of tetrafluoroethylene, hexafluoropropylene, vinylidene fluoride, and chlorotrifluoroethylene.

Embodiment 17

The method of any one of embodiments 14-16, wherein the second fluoroolefin is selected from at least one of tetrafluoroethylene, hexafluoropropylene, vinylidene fluoride, and chlorotrifluoroethylene.

Embodiment 18

The method of any one of embodiments 14-17, wherein an even numbered perfluoroorganyl diacid difluorides are synthesized by inserting a first perfluroolefin into a difluorosulfuryl peroxide to form a perfluoroorganyl bisfluorosulfate and reacting the perfluoroorganyl bisfluorosulfate with a catalyst to form a corresponding diacid difluoride.

Embodiment 19

The method of any one of embodiments 14-18, wherein the catalyst is selected from nitrogen containing bases or metal fluorides MF wherein M is Li, Na, K, or Cs.

Embodiment 20

The method of any one of embodiments 14-19, wherein the halogenated fluorinated ether-containing compound has the structure selected from at least one of:

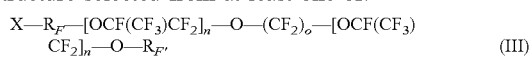
(III)

wherein X is selected from I, Br and Cl; $R_F$ is $CF_2CF_2$ or $CF_2CF_2CF_2$; n is an integer from 0-3; o is an integer from 2-6, 8, and 10; and $R_{F'}$ is CF=$CF_2$ and $CF_2CF$=$CF_2$; and

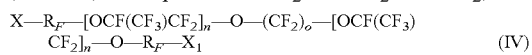
(IV)

wherein X and $X_1$ are independently selected from I, Br and Cl; $R_F$ is independently $CF_2$—$CF_2$, $CF(CF_3)CF_2$, $CFClCF_2$, or $CH_2CF_2$; n is an integer from 0-3; o is an integer from 2-6, 8, and 10.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: A=amps, b.p.=boiling point, g=gram, h=hour, kg=kilograms, min=minutes, mol=mole, cm=centimeter, mbar=millibar, mm=millimeter, mL=milliliter, L=liter, psi=pressure per square inch, MPa=megaPascals, and wt=weight.

Example 1

Synthesis of $FSO_2$—O—O—$SO_2F$ $FSO_3H$ was electrolyzed in a 10 L double-walled glass-lined cell equipped with steel cathodes and glassy carbon anodes (surface of electrodes was 720 cm²). The electrolyte was prepared in the cell by dissolving NaCl (410 g, 7.0 mol) in $FSO_3H$ (13.1 kg, 8.5 L, 130.9 mol) and by removing the formed HCl with dry nitrogen under intensive stirring. A current of 70 A at 56° C. for 2 h was applied to the cell. The amount of the resulting peroxide (517 g, 2.6 mol) was calculated (Faraday's law). The calculated value was in accordance with the result by titration with KI (2 mL of the electrolyte was added to an ice-cooled solution of KI and the resulting iodine was determined with a solution of thiosulfate).

Synthesis of $ICF_2CF_2OSO_2F$

An equimolar amount of iodine (660 g, 2.6 mol) at a temperature range of 20-65° C. was added to the $FSO_2$—O—O—$SO_2F$ prepared above. Then, TFE was slowly introduced into the cell at <50° C. After feeding an equimolar amount of TFE (260 g, 2.6 mol) during 1 h, the bottom layer was separated and distilled. $ICF_2CF_2OSO_2F$ was produced in 85% yield (720 g, 2.2 mol; b.p. 100° C.).

Synthesis of $ICF_2C(O)F$ $ICF_2C(O)F$ was produced from $ICF_2CF_2OSO_2F$ (350 g, 1.1 mol) in the presence of CsF (15 g, 0.1 mol) and was heated up to 90° C. for 3 hours. $ICF_2C(O)F$ was collected in 91% yield (224 g, 1.0 mol; b.p. 39 to 41° C.).

Synthesis of $ICF_2CF_2OCF$=$CF_2$ and $ICF_2CF_2OCF(CF_3)CF_2OCF$=$CF_2$;

CsF (3.1 g, 0.02 mol, which was dried at 110° C. in vacuum before usage), diglyme (150 mL) and $ICF_2COF$ (156.7 g, 0.70 mol) were placed in a steel vessel. Then, HFPO (121 g, 0.73 mol) was added at −20° C. The reaction mixture was stirred at room temperature overnight. The bottom layer was separated and distilled. A mixture of $ICF_2CF_2OCF(CF_3)C(O)F$ and $ICF_2CF_2OCF(CF_3)CF_2OCF(CF_3)C(O)F$ was obtained which was subsequently heated in the presence of $K_2CO_3$ (430 g, 3.1 mol) in diglyme (800 mL) at 150 to 180° C. The yield of $ICF_2CF_2OCF$=$CF_2$ (68 g, 0.21 mol; b.p. 102° C.) and $ICF_2CF_2OCF(CF_3)CF_2OCF$=$CF_2$ (172 g, 0.35 mol; b.p. 126° C.) was 30% and 50%, respectively (yield calculated based on the amount of material collected versus the theoretical amount formed assuming 100% conversion).

Example 2: Synthesis of $ICF_2CF_2OCF_2CF_2I$

A steel vessel was charged with a suspension of KF (32 g, 0.55 mol; dried over night at 190° C. under vacuum) in diglyme (200 mL) at room temperature. The mixture was cooled to −20° C. and ICF$_2$C(O)F (112 g, 0.5 mol) from above was added. The mixture was warmed up to ambient temperature and was stirred for one hour. The mixture was cooled to −20° C. again and consecutively I$_2$ (140 g, 0.55 mol) and TFE were added at 4.5 bar. The progress of the reaction was followed by the drop of the pressure. TFE was added until the consumption of TFE was negligible. The remaining TFE and other volatile compounds were removed and the reaction mixture was washed with aqueous solutions of Na$_2$S$_2$O$_3$ and NaHCO$_3$, dried and distilled. ICF$_2$CF$_2$OCF$_2$CF$_2$I was isolated in 31% yield (72 g, 0.15 mol; b.p. 136° C.).

Example 3

Synthesis of ICF$_2$CF$_2$CN:

A stainless steel vessel was charged with NaCN (25.1 g, 0.51 mol) and CH$_3$CN (1189.4 g, 29.0 mol) and TFE (32 g, 0.32 mol) was added at 10° C. The mixture was warmed up to 20° C. for 1 h and then cooled to 10° C. Then, a solution of iodine (25.6 g, 0.10 mol) in CH$_3$CN (403 g, 9.8 mol) was added. The mixture was stirred overnight at 60° C. The mixture was cooled to 20° C. BF$_3$.THF (7.8 g, 0.06 mol) was added and the mixture was heated over night at 60° C. again. ICF$_2$CF$_2$CN was formed in 43% yield (35.4 g, 0.14 mol; b.p. 60° C.).

$^{19}$F NMR(CH$_3$CN, RT; ppm): −55.0 I—CF$_2$—; −109.4 —CF$_2$—CN; GC-MS (m/e): 252.9 (ICF$_2$CF$_2$CN$^+$), 176.9 (ICF$_2$$^+$), 127.0 (I$^+$), 126.0 (NCCF$_2$CF$_2$$^+$), 107.0 (CF$_2$CFCN$^+$), 100.0 (C$_2$F$_4$$^+$), 76.0 (NCCF$_2$$^+$).

Example 4

Syntheses of FSO$_2$O—(CF$_2$CF$_2$)$_x$—OSO$_2$F

TFE was introduced in a solution of FSO$_2$—O—O—SO$_2$F in FSO$_3$H under vigorous stirring in the above mentioned glasslined cell.

The electrolyte was prepared by dissolving NaCl (360 g, 6.2 mol) in FSO$_3$H (12.77 kg, 127.6 mol) and blowing out the HCl formed with dry nitrogen under intensive stirring.

The reaction with TFE was carried out at 35 to 60° C., electric voltage 15 V, current of 56 A and current density 78 mA/cm. TFE was injected into the cell at the rate of 200 g/h (2 mol/h; in total: 1.51 kg, 15.1 mol). After the reaction, a biphasic system resulted. The lower (product) phase was separated (4.14 kg) and after intensively washing with water, a clear yellowness phase (3.75 kg) was isolated. GC analysis provided the following distribution of FSO$_2$O—(CF$_2$CF$_2$)$_x$—OSO$_2$F: x=1: 3.9, x=2: 35.8, x=3: 33.2, x=4: 16.9, x=5: 6.3.

Synthesis of CF$_2$=CFO(CF$_2$)$_4$OCF=CF$_2$

The fractionated FSO$_2$O—(CF$_2$CF$_2$)$_x$—OSO$_2$F wherein x=2 from above was converted to F(O)C(CF$_2$)$_2$C(O)F using CsF at 50° C.

In a steel vessel were placed CsF (13 g, 0.09 mol) and F(O)C(CF$_2$)$_2$C(O)F (213.4 g, 1.1 mol) in diglyme (166 mL) at 0° C. The steel vessel was cooled to −18° C. Afterwards, HFPO (432 g, 2.6 mol) was added and the mixture was stirred at ambient temperature for 13 h. A biphasic mixture was obtained. The bottom layer was separated and distilled. The obtained F(O)C(CF$_3$)CFO(CF$_2$)$_4$OCF(CF$_3$)C(O)F was subsequently heated in the presence of K$_2$CO$_3$ (1.2 kg, 9 mol) in diglyme (2.5 L) at 150 to 180° C. The yield of CF$_2$=CFO(CF$_2$)$_4$OCF=CF$_2$ was 55% (240 g, 0.61 mol; b.p. 111° C. at 950 mbar).

$^{19}$F NMR(CDCl$_3$, RT; ppm): −86.6 (m, 4F), −116.0 (dd, 2F), −123.8 (ddt, 2F), −126.9 (m, 4F), −137.2 (ddt, 2F)

Synthesis of ICF$_2$CF$_2$O(CF$_2$)$_4$OCF$_2$CF$_2$I

In a steel vessel were placed CF$_2$=CFO(CF$_2$)$_4$OCF=CF$_2$ (169.5 g, 0.43 mol), I$_2$ (88.7 g, 0.35 mol), and IF$_5$ (155.3 g, 0.70 mol). The mixture was heated at 138° C. for 16 h. After cooling to room temperature, volatile byproducts were removed by flushing with nitrogen and the remaining liquid was carefully poured into ice-water. After intensively washing with ice-water and sodium bicarbonate solution, the liquid was dried over MgSO$_4$ and distilled. The isolated yield was 56% (164.6 g, 0.24 mol; b.p. 70° C. at 5.4 mbar).

Example 5

Synthesis of ICF$_2$CF$_2$O(CF$_2$)$_4$OCF=CF$_2$

In a steel vessel were placed CF$_2$=CFO(CF$_2$)$_4$OCF=CF$_2$ (161.6 g, 0.41 mol), I$_2$ (40.6 g, 0.16 mol), and IF$_5$ (71.0 g, 0.32 mol). The mixture was heated at 142° C. for 16 h. After cooling to room temperature, volatile byproducts were removed by flushing with nitrogen and the remaining liquid was carefully poured into ice-water. After intensively washing with ice-water and sodium bicarbonate solution, the liquid was dried over MgSO$_4$ and distilled. The isolated yield was 51% (113.4 g, 0.21 mol; b.p. 59° C. at 5.4 mbar)

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A method of making a halogenated fluorinated ether-containing compound from a fluoroolefin, the method comprising:
   (i) halogenating a difluorosulfuryl peroxide followed by reaction with a first fluoroolefin to form a halogenated fluoroorganyl acid fluoride;
   (ii) reacting the halogenated fluoroorganyl acid fluoride with first compound selected from at least one of:
   (a) a second fluoroolefin in the presence of a halogen containing compound to form the halogenated fluorinated ether-containing compound; and
   (b) HFPO to form a corresponding acid fluoride and converting the corresponding acid fluoride into the halogenated fluorinated ether-containing compound.

2. The method of claim 1, wherein converting the corresponding acid fluoride is selected from:
   (i) reacting the corresponding acid fluoride with a third fluoroolefin in the presence of a halogen containing compound to form the halogenated fluorinated ether-containing compound;
   (ii) pyrolyzing the corresponding acid fluoride to form a vinyl ether; then reacting the vinyl ether with an interhalogen to form the halogenated fluorinated ether-containing compound;
   (iii) reacting the corresponding acid fluoride with CF$_2$=CF—CF$_2$—OSO$_2$F to form the halogenated fluorinated ether-containing compound; or
   (iv) reacting the corresponding acid fluoride with LiI to form the halogenated fluorinated ether-containing compound.

3. The method of claim 1, further comprising reacting the corresponding acid fluoride with HFPO to form an elongated acid fluoride, which is then converted into the halogenated fluorinated ether-containing compound.

4. The method of claim 1, wherein the halogenated fluorinated ether-containing compound has the structure selected from at least one of:

$$X-CFYCF_2-[OCF(CF_3)CF_2]_n-O-R_F \quad (I)$$

wherein X is selected from Br, Cl and I; Y is F or $CF_3$; n is an integer from 0-3 and $R_F$ is $CF=CF_2$ and $CF_2CF=CF_2$; and $$X-CFYCF_2-[OCF(CF_3)CF_2]_n-O-R_{F'}-X_1 \quad (II)$$

wherein X and $X_1$ are independently selected from Br, Cl and I; Y is F or $CF_3$; $R_{F'}$ is selected from $CF_2CF_2$, $CF(CF_3)CF_2$, $CFClCF_2$, or $CH_2CF_2$; and n is an integer from 1-3.

5. A method of making a halogenated fluorinated ether-containing compound from a fluoroolefin, the method comprising:
(i) forming 2,2,3,3-tetrafluoro-3-halogenopropanenitrile using a cyanide containing compound and TFE wherein the forming is selected from:
  a) adding XCN to TFE wherein X is I, Br or Cl; and
  b) adding MCN to TFE wherein M is an alkali metal followed by contact with a halogen containing compound;
(ii) converting the 2,2,3,3-tetrafluoro-3-halogenopropanenitrile to 2,2,3,3-tetrafluoro-3-halogenopropanoyl fluoride;
(iii) reacting the 2,2,3,3-tetrafluoro-3-halogenopropanoyl fluoride with a first compound selected from at least one of
(a) a fluoroolefin in the presence of a halogen containing compound to form the halogenated fluorinated ether-containing compound and
(b) HFPO to form the corresponding acid fluoride and converting the corresponding acid fluoride into a halogenated fluorinated ether-containing compound.

6. The method of claim 5, wherein the converting of the corresponding acid fluoride is selected from:
(a) reacting the corresponding acid fluoride with a second compound selected from at least one of (i) a third fluoroolefin in the presence of a halogen containing compound to form the corresponding halogenated ether-containing compound and (ii) HFPO to form the corresponding acid fluoride;
(b) pyrolizing the corresponding acid fluoride to form a vinyl ether; then reacting the vinyl ether with an interhalogen to form the halogenated fluorinated ether-containing compound;
(c) reacting the corresponding acid fluoride with $CF_2=CF-CF_2-OSO_2F$ to form the the halogenated fluorinated ether-containing compound; or
(d) reacting the corresponding acid fluoride with LiI to form the halogenated fluorinated ether-containing compound.

7. The method of claim 5, wherein the halogenated fluorinated ether-containing compound has the structure selected from at least one of:

$$X-CF_2CF_2CF_2-[OCF(CF_3)CF_2]_n-O-R_F \quad (I)$$

wherein X is selected from I, Br and Cl, n is an integer from 0-3; and $R_F$ is $CF=CF_2$ and $CF_2CF=CF_2$; and $$X-CF_2CF_2CF_2-[OCF(CF_3)CF_2]_n-O-R_{F'}-X_1 \quad (II)$$

wherein X and $X_1$ are independently selected from I, Br and Cl; $R_{F'}$ is selected from $CF_2CF_2$, $CFClCF_2$, or $CH_2CF_2$; and n is an integer from 0-3.

8. A method of making halogenated fluorinated ether-containing compound from a fluoroolefin, the method comprising:

(i) reacting a perfluoroorganyl diacid difluoride with a first compound selected from at least one of
(a) a first fluoroolefin in the presence of a halogen containing compound to form the halogenated fluorinated ether-containing compound; and
(b) HFPO to form the corresponding diacid difluoride and converting the corresponding diacid difluoride into the halogenated fluorinated ether-containing compound.

9. The method of claim 8, wherein the converting step is selected from:
(i) reacting the corresponding diacid difluoride with a second compound selected from at least one of
(a) a second fluoroolefin in the presence of a halogen containing compound to form the halogenated fluorinated ether-containing compound and
(b) reacting the corresponding acid fluoride with HFPO to form an acid fluoride
(ii) pyrolizing the corresponding acid fluoride to form a vinyl ether; then reacting the vinyl ether with an interhalogen to form the halogenated fluorinated ether-containing compound;
(iii) reacting the corresponding acid fluoride with $CF_2=CF-CF_2-OSO_2F$ to form the halogenated fluorinated ether-containing compound; or
(iv) reacting the corresponding acid fluoride with LiI to form the halogenated fluorinated ether-containing compound.

10. The method of claim 8, wherein the halogenated fluorinated ether-containing compound has the structure selected from at least one of:

$$X-R_F-[OCF(CF_3)CF_2]_n-O-(CF_2)_o-[OCF(CF_3)CF_2]_n-O-R_{F'} \quad (III)$$

wherein X is selected from I, Br and Cl; $R_F$ is $CF_2CF_2$ or $CF_2CF_2CF_2$; n is an integer from 0-3; o is an integer from 2-6, 8, and 10; and $R_{F'}$ is $CF=CF_2$ and $CF_2CF=CF_2$; and $$X-R_F-[OCF(CF_3)CF_2]_n-O-(CF_2)_o-[OCF(CF_3)CF_2]_n-O-R_{F'}-X_1 \quad (IV)$$

wherein X and $X_1$ are independently selected from I, Br and Cl; $R_{F'}$ is independently $CF_2CF_2$, $CF(CF_3)CF_2$, $CFClCF_2$, or $CH_2CF_2$; n is an integer from 0-3; o is an integer from 2-6, 8, and 10.

11. The method of claim 1, wherein the first fluoroolefin is selected from at least one of tetrafluoroethylene, hexafluoropropylene, and chlorotrifluoroethylene.

12. The method of claim 1, wherein the second fluoroolefin is selected from at least one of tetrafluoroethylene, hexafluoropropylene, vinylidene fluoride, and chlorotrifluoroethylene.

13. The method of claim 2, wherein the third fluoroolefin is selected from at least one of tetrafluoroethylene, hexafluoropropylene, vinylidene fluoride, and chlorotrifluoroethylene.

14. The method of claim 6, wherein the second fluoroolefin is selected from at least one of tetrafluoroethylene, hexafluoropropylene, vinylidene fluoride, and chlorotrifluoroethylene.

15. The method of claim 6, wherein the third fluoroolefin is selected from at least one of tetrafluoroethylene, hexafluoropropylene, vinylidene fluoride, and chlorotrifluoroethylene.

16. The method of claim 5, further comprising reacting the corresponding acid fluoride with HFPO to form an elongated acid fluoride, which is then converted into the halogenated fluorinated ether-containing compound.

17. The method of claim 8, wherein the first fluoroolefin is selected from at least one of tetrafluoroethylene, hexafluoropropylene, vinylidene fluoride, and chlorotrifluoroethylene.

18. The method of claim 9, wherein the second fluoroolefin is selected from at least one of tetrafluoroethylene, hexafluoropropylene, vinylidene fluoride, and chlorotrifluoroethylene.

19. The method of claim 8, wherein an even numbered perfluoroorganyl diacid difluorides are synthesized by inserting a first perfluroolefin into a difluorosulfuryl peroxide to form a perfluoroorganyl bisfluorosulfate and reacting the perfluoroorganyl bisfluorosulfate with a catalyst to form a corresponding diacid difluoride.

20. The method of claim 19, wherein the catalyst is selected from nitrogen containing bases or metal fluorides MF wherein M is Li, Na, K, or Cs.

* * * * *

UNITED STATES PATENT AND TRADEMARK OFFICE
CERTIFICATE OF CORRECTION

PATENT NO. : 9,828,320 B2  
APPLICATION NO. : 15/529104  
DATED : November 28, 2017  
INVENTOR(S) : Klaus Hintzer Page 1 of 2

It is certified that error appears in the above-identified patent and that said Letters Patent is hereby corrected as shown below:

In the Specification

Column 4,  
Line 15, delete "pyrolized" and insert -- pyrolyzed --, therefor.

Column 6,  
Line 56, delete "pyrolized" and insert -- pyrolyzed --, therefor.

Column 8,  
Line 40, delete "pyrolized" and insert -- pyrolyzed --, therefor.  
Line 54, delete "$(OCF_2)_o$" and insert -- $(CF_2)_o$ --, therefor.

Column 9,  
Line 9, delete "$CF_2\text{---}CF_2$," and insert -- $CF_2\text{=}CF_2$, --, therefor.

Column 12,  
Line 1, delete "pyrolizing" and insert -- pyrolyzing --, therefor.  
Line 6, delete "the the" and insert -- the --, therefor.  
Line 32, after "compound" insert -- . --.

Column 13,  
Line 8, delete "pyrolizing" and insert -- pyrolyzing --, therefor.  
Line 35, delete "perfluroolefin" and insert -- perfluoroolefin --, therefor.

Column 14,  
Line 47, delete "$CF_2$;" and insert -- $CF_2$: --, therefor.

Column 16,  
Line 2, after "2F)" insert -- . --.  
Line 26, after "mbar)" insert -- . --.

Signed and Sealed this  
Twenty-second Day of May, 2018

Andrei Iancu  
*Director of the United States Patent and Trademark Office*

CERTIFICATE OF CORRECTION (continued)
U.S. Pat. No. 9,828,320 B2

In the Claims

<u>Column 17</u>,
Line 44, in Claim 6, delete "pyrolizing" and insert -- pyrolyzing --, therefor.
Line 48, in Claim 6, delete "the the" and insert -- the --, therefor.

<u>Column 18</u>,
Line 19, in Claim 9, delete "pyrolizing" and insert -- pyrolyzing --, therefor.

<u>Column 19</u>,
Line 11, in Claim 19, delete "perfluroolefin" and insert -- perfluoroolefin --, therefor.